United States Patent [19]

Meinert et al.

[11] Patent Number: 5,091,064
[45] Date of Patent: Feb. 25, 1992

[54] METHOD FOR PREPARING PERFLUORINATED HETEROCYCLIC COMPOUNDS, AND COMPOUNDS PREPARED BY THIS METHOD

[75] Inventors: Hasso Meinert, Ulm; Rudolf Fackler, Senden; Juergen Mader, Ulm; Peter Reuter, Ulm-Lehr, all of Fed. Rep. of Germany

[73] Assignee: Kali-Chemie AG, Hanover, Fed. Rep. of Germany

[21] Appl. No.: 572,550

[22] Filed: Aug. 27, 1990

[30] Foreign Application Priority Data

Aug. 30, 1989 [DE] Fed. Rep. of Germany ....... 3928692
Dec. 15, 1989 [DE] Fed. Rep. of Germany ....... 3941515

[51] Int. Cl.$^5$ ............................................ C25B 3/08
[52] U.S. Cl. .................... 204/59 F; 544/106; 546/184; 548/400
[58] Field of Search ............... 204/59 F; 544/106; 546/184; 548/400

[56] References Cited

U.S. PATENT DOCUMENTS

| | | | |
|---|---|---|---|
| 3,950,235 | 4/1976 | Benninger | 204/59 F |
| 4,231,849 | 11/1980 | Hutchinson et al. | 204/59 F |
| 4,235,782 | 11/1980 | Abe et al. | 204/59 F |
| 4,530,926 | 7/1985 | Yokoyama et al. | 514/214 |
| 4,534,978 | 8/1985 | Yokoyama et al. | 514/429 |
| 4,766,261 | 8/1988 | Bierl | 570/179 |

FOREIGN PATENT DOCUMENTS

77114 4/1983 European Pat. Off. .
275079 1/1990 Fed. Rep. of Germany .

OTHER PUBLICATIONS

Obraztsov, V. V. "Study of Physicochemical Properties of Fluorocarbon Inducers of Cytochrome P450 in Rat Liver, Endoplasmic Reticulum Membrane," Biokhimiia (Russ), 53(4), 613–619 (1988).
Chemical Abstracts, vol. 109, Abstract 1969d and p. 5928CS (1988).
Naito et al., J. Fluorine Chem., 26, 485–97 (1984).
Moore et al., J. Fluorine Chem., 32, 41–76 (1986).
Ono et al., J. Fluorine Chem., 43, 67–85 (1989).

*Primary Examiner*—John Niebling
*Assistant Examiner*—Steven P. Marquis
*Attorney, Agent, or Firm*—Foley & Lardner

[57] ABSTRACT

A method for preparing perfluorinated heterocyclic compounds corresponding to the formulas Ia and Ib

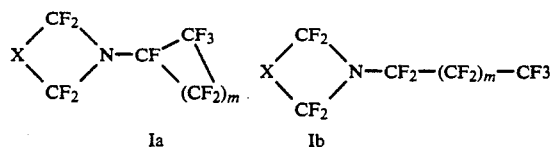

wherein
m represents 3 or 4, and
x is a $-CF_2-O-CF_2-$ group, a $-CF_2-CF_2-CF_2-$ group, or a $-CF(CF_3)-CF_2-$ group, and their mixtures, and the perfluoro-N-cyclohexylmorpholine prepared by this method. The compounds are obtained by electrochemical perfluorination starting from corresponding cycloalkenyl derivatives, and they can be used for preparing medically usable aqueous emulsions, e.g. blood substitutes.

16 Claims, No Drawings

METHOD FOR PREPARING PERFLUORINATED HETEROCYCLIC COMPOUNDS, AND COMPOUNDS PREPARED BY THIS METHOD

BACKGROUND OF THE INVENTION

The present invention relates to a method for preparing perfluorinated, heterocyclically substituted cycloalkyl compounds and mixtures thereof with corresponding n-alkyl compounds starting from corresponding unfluorinated cycloalkenyl compounds. The present invention further relates to new perfluorinated compounds prepared for the first time by the method of the invention, and to the use of these new compounds.

The compounds which can be prepared in accordance with the invention are of the so-called perfluorocarbon type. Perfluorocarbons are perfluorinated organic carbons which are liquid to waxy at room temperature under standard pressure. They are water-insoluble, biologically inert compounds which consist of carbon and fluorine, and in some cases may also contain hetero atoms such as nitrogen or oxygen. Such compounds are disclosed, for example, in published European Patent Application Nos. EP 77,114; EP 99,652; and EP 151,697. The perfluorocarbon molecules are outstandingly shielded by a uniform shell of fluorine atoms. Therefore, perfluorocarbons are extraordinarily inert chemically and physiologically, and thus nontoxic. Due to their extremely low intermolecular forces, perfluorocarbons have low boiling points in proportion to their molecular weights, and an extraordinarily low surface tension. The very weak intermolecular forces also are responsible for the ability of the perfluorocarbons to dissolve large amounts of gases such as oxygen and carbon dioxide. Due to these properties, especially the ability to physically dissolve and transport oxygen, perfluorocarbons have been used in medicine for preparing oxygen-transporting aqueous emulsions of perfluorocarbons, which are used, for example, as blood substitutes or perfusion media. Further, perfluorocarbons are also suitable for use in other technical fields in which nontoxic and chemically inert liquid or waxy substances are needed, or in which inert substances with the ability to dissolve gases are needed.

Previously known methods for preparing perfluorinated, heterocyclically substituted cycloalkyl compounds start from corresponding saturated, unfluorinated cycloalkyl compounds which must be obtained by complex preparation methods. In comparison with such processes, the method of the invention has the advantage that it uses starting materials which are easily accessible through a small number of reaction steps.

SUMMARY OF THE INVENTION

The object of the present invention is to develop an economical and improved method for preparing perfluorinated, heterocyclically substituted cycloalkyl compounds by which new compounds of this type also are made available.

These and other objects of the invention are achieved by providing a method for preparing compounds corresponding to the formulas Ia and Ib:

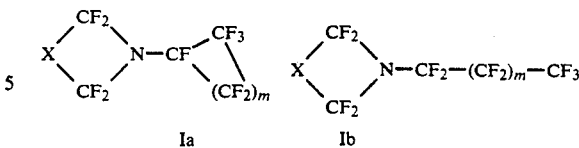

wherein m is 3 or 4 and X is a —$CF_2$—O—$CF_2$— group, a —$CF_2$—$CF_2$—$CF_2$— group or a —$CF(CF_3)$—$CF_2$— group, or mixtures thereof, said method comprising the steps of:

a) electrolyzing a solution of a compound corresponding to the formula II:

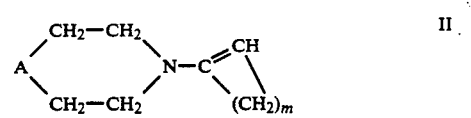

wherein m has the above meaning and A represents oxygen or a —$CH_2$— group, in liquid hydrogen fluoride, and separating a raw reaction product containing perfluorinated compounds of formulas Ia and Ib plus partially fluorinated by-products;

b) treating said raw reaction product with an alkali metal or alkaline earth metal base in the presence of water at an elevated temperature sufficient to decompose the partially fluorinated by-products; and c) isolating a mixture of the compounds of formulas Ia and Ib from the treated reaction product from step b).

According to a further aspect of the invention, the objects of the invention are achieved by providing a perfluoro-N-cyclohexylmorpholine of formula I'a:

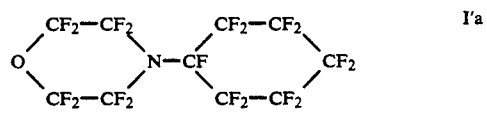

or a mixture thereof with a perfluoro-N-n-hexylmorpholine of formula I'b:

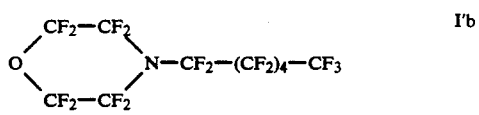

According to further aspects of the invention, the perfluorocompounds are separated into isomers using molecular sieves.

DETAILED DESCRIPTION OF PREFERRED EMBODIMENTS

It has been found that perfluorinated, heterocyclically substituted cycloalkyl compounds and corresponding n-hexyl compounds can be obtained in good yields by electrochemical fluorination of corresponding unfluorinated, unsaturated cycloalkylene compounds.

The subject of the present invention is a method for preparing compounds of the general formulas Ia and Ib:

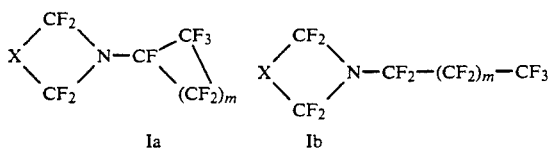

wherein m is 3 or 4 and X is a —CF₂—O—CF₂— group, a —CF₂—CF₂—CF₂— group or a —CF(CF₃)—CF₂— group, or mixtures thereof, characterized in that a) a solution of compounds of the general formula II

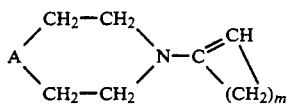

wherein m has the above meaning and A represents oxygen or a —CH₂— group, is electrolyzed in liquid hydrogen fluoride, and a raw reaction product containing the perfluorinated compounds of formulas Ia and Ib plus only partially fluorinated by-products is separated;

b) the raw reaction product is treated with an alkali metal or alkaline earth metal base, especially an alkali metal or alkaline earth metal hydroxide, in the presence of water and, optionally, a lower aliphatic primary or secondary amine at an elevated temperature sufficient to decompose only partially fluorinated by-products;

c) a mixture of the compounds of formulas Ia and Ib is isolated from a reaction mixture obtained in process step b), and this is separated, if desired, into the compounds of formulas Ia and Ib, and d) if desired, isomer mixtures of compounds Ia or Ib, wherein X is a —CF₂—CF₂CF₂— group and m has the above meaning, and compounds of formulas Ia or Ib which are isomeric therewith, wherein X represents a —CF(CF₃)—CF₂— group, are separated into the individual isomers.

It is considered surprising that compounds of formula II can be reacted to produce corresponding mixtures of perfluorinated compounds of formulas Ia and Ib without cleaving the molecule at the double bond and forming cleavage products and/or polymeric derivatives thereof.

The invention also includes the new perfluoro-N-cyclohexylmorpholine of formula I'a, which has been prepared for the first time, and mixtures thereof with perfluoro-N-n-hexylmorpholine of formula I'b:

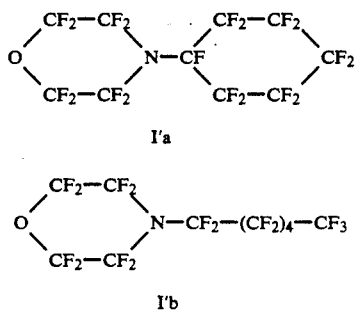

Due to their chemical and physiological inertness and their ability to dissolve gases such as oxygen and carbon dioxide, the perfluorinated heterocyclic compounds prepared according to the invention are usable for the same uses as mentioned above for perfluorocarbons.

The compound of formula I'a is characterized by an especially desirable profile of properties, on the basis of which it and its mixtures with compound I'b are especially suitable for preparing aqueous perfluorocarbon emulsions capable of transporting oxygen, which can be used in medicine, for example as blood substitutes or also for perfusion and storage of organs in transplant surgery.

Perfluorocarbons are hydrophobic, water-immiscible substances. Therefore, they cannot be introduced as such into the circulatory system, but only in the form of physiologically acceptable aqueous emulsions. Such emulsions are prepared conventionally by using a physiologically acceptable emulsifier and constitute oil-in-water type emulsions.

In addition to good physiological compatibility, e.g., osmotic and oncotic (colloid osmotic) pressures, rheological properties and pH constancy similar to those of normal blood, and a good capacity for dissolving oxygen, it is important for emulsions usable as blood substitutes that they have an appropriate residence time in the circulatory system, and subsequently are eliminated as completely as possible and without excessive retention in organs. Half-lives in the body of about one week to one month, especially of about two to four weeks, are considered advantageous. Also it is important that the emulsions have sufficient stability against growth of the oil phase particles.

Due to their chemical inertness, perfluorocarbons are virtually not metabolized at all in the body and are excreted unchanged in the breath or through the skin. The rate of excretion of individual perfluorocarbons differs greatly and can vary from a few days to several years. The rate of excretion of the individual substances depends greatly on their vapor pressure and on their solubility in slightly polar media, since the rate of permeation of the perfluorocarbons through the alveolar membranes depends on these parameters.

The critical temperature of dissolution in n-hexane (=CTSH) can serve as a measure of the lipophilia of the perfluorocarbons, that is, the temperature at which the particular perfluorocarbon dissolves in an equal amount of n-hexane. The determination of the CTSH of a perfluorocarbon is therefore an in vitro test method which represents a good index of the retention time of the perfluorocarbon in the body. An adequate lipophilia and a sufficiently high vapor pressure are advantageous for a satisfactory exhalation rate.

The compound of formula Ia' is especially suited as an oxygen carrying component of perfluorocarbon emulsions suitable as blood substitutes, since in addition to a high capacity for dissolving oxygen, it has both good emulsifiability and a CTSH and vapor pressure favorable to a good half-life in the body with a good rate of elimination.

In accordance with the invention, mixtures of compounds of formula Ia and the by-products of formula Ib are prepared by electrochemical fluorination of unsaturated compounds of formula II by electrolyzing solutions of the compounds of formula II in liquid hydrogen fluoride. Advantageously, solutions of 4 to 30 wt.-%, preferably 5 to 10 wt.-%, of a compound of formula II in liquid hydrogen fluoride are used for the process. The electrolysis advantageously takes place in an electrolysis cell at temperatures between −25 and +10° C., preferably between −5 and +5° C.; at an anode current density of 2–30 mA/cm² and a cell voltage of 3–10, especially 4–8 volts. For the electrolysis it may prove helpful to feed the electrolyte to the vicinity of the electrodes again and again by continuously stirring the contents of the cell.

Since electrochemical fluorination in liquid hydrogen fluoride is a very high-energy process, in which the perfluorination often is associated with considerable side reactions, it was not to be expected that unsaturated bicyclic compounds of formula II could be-perfluorinated by electrochemical fluorination with a yield sufficient for the practical production of compounds Ia. Rather, it would have been expected for cleavage at the C=C double bonds of the cycloalkylene ring and also the cleavage of carbon-to-hetero atom bonds to occur. Electrochemical perfluorination of the compounds of formula II is successful in accordance with the invention, with satisfactory yields, if it is performed in the above-stated, relatively low temperature range and at the above-stated relatively low cell voltage.

For further processing, the raw reaction product which settles as a heavy phase on the bottom of the electrolysis cell is separated and, to decompose any only partially fluorinated by-products, it is subjected to treatment with an alkali metal or alkaline earth metal hydroxide, in the presence of water and, optionally, a lower aliphatic primary or secondary amine, at a temperature sufficiently high to decompose any partially fluorinated by-products. This process step can be performed under known reaction conditions, for example, in a manner analogous to the methods described in published European Patent Application Nos. EP 99,652 and EP 151,697. It has proved advantageous to treat the raw reaction product with a 6N to 10N aqueous alkali metal hydroxide solution, especially potassium hydroxide solution, and a lower aliphatic amine at elevated temperature, preferably the boiling temperature of the reaction mixture. Thus, the reaction mixture can be heated to boiling with refluxing for a period of from several hours up to 8 days. Suitable lower aliphatic amines are lower primary or secondary amines or diamines which are liquid at room temperature, preferably secondary amines such as, for example, dialkylamines with up to 5 carbon atoms in their alkyl moieties, or hexamethylene diamine or also cyclic amines such as piperidine. Preferably a dibutyl amine, such as, for example, diisobutyl amine, is used.

From the resultant reaction mixture, mixtures of compounds of formula Ia and Ib can be isolated in a known manner, for example by fractional distillation. The mixtures, in which the compounds of formula Ia generally predominate, can be separated in a known manner, if desired, into the compounds of formulas Ia and Ib.

The mixtures separated from the reaction mixture by fractional distillation are free from any non-perfluorinated products. However, they may contain, in addition to the principal product of formula Ia, some likewise perfluorinated, and therefore chemically and physiologically inert, by-products. In particular, they may contain perfluorinated by-products which have a molecular weight similar to that of the principal product and therefore boil in the same temperature range as the principal product. The presence of such perfluorinated by-products, however, does not impair the proper use of the compounds, so that the products purified by distillation can generally be used without further purification.

Under the conditions of the electrochemical perfluorination of compounds of formula II, a ring contraction occurs to some extent in compounds containing piperidine rings, so that in addition to compounds of formulas Ia and Ib, in which X represents a —CF$_2$—CF$_2$—CF$_2$—group, compounds isomeric therewith, in which X represents a —CF(CF$_3$)—CF$_2$— group, are obtained to a lesser extent. These isomer mixtures of compounds of formula Ia and/or Ib can be used in the same manner as pure compounds of formulas Ia and/or Ib.

If desired, the isomer mixtures can be separated into their individual isomers. It is desirable to perform a separation of mixtures of compounds Ia and Ib and/or a separation of isomers by adsorption/desorption on molecular sieves, preferably molecular sieves with a pore size of 5 to 6 Å. Suitable molecular sieves include, for example, inorganic aluminosilicates, zeolites and silicalites (=silicon dioxide with a suitable pore size). Zeolites are preferably used. Inorganic molecular sieves are generally suitable for separating compounds containing only unsubstituted perfluorinated rings from by-products containing perfluoroalkyl substituents. Depending on the size of the perfluoroalkyl substituents, molecular sieves with pore sizes between 5 and 6.5 Å are selected for this purpose. Isomer mixtures can also be separated in a known manner by preparative gas chromatography.

The starting compounds of formula II are known, or they can be prepared by known methods or in a manner analogous to known methods.

The compounds prepared in accordance with the invention, especially compound I'a or its mixtures with compound I'b can be made in a known manner into medically usable aqueous emulsions. Such emulsions are oil-in-water type emulsions which contain 5 to 50, especially 15 to 25, preferably about 20, grams of perfluorinated compounds, i.e. compounds of formula Ia or Ib or their mixtures, and optionally other physiologically acceptable perfluorocarbons, per 100 milliliters of emulsion, and a physiologically acceptable emulsifier, optionally further physiologically acceptable adjuvants. It may be desirable to use perfluorocarbon mixtures which contain a small proportion of relatively high-boiling compounds.

Physiologically acceptable emulsifiers which are themselves nontoxic, have no hemolysis-causing properties, and otherwise do not have any interaction with components of natural blood and which are completely eliminated from the body or metabolized to nontoxic metabolites, are suitable for use as the emulsifiers. Suitable emulsifiers include, for example, natural phospholipids such as egg lecithins or soya lecithins, and albumins. Also suitable are physiologically acceptable, nonionic emulsifiers of the ethylene oxide-propylene oxide copolymer type, e.g., copolymers with a molecular weight in the range from 8000 to 8500. Such emulsifiers are commercially, available, for example under the trademark Pluronic TM, from Wyandotte Chemicals Corp. The emulsifiers can be contained in the emulsions in accordance with the invention in a concentration of, for example, 2 to 7 grams per 100 milliliters of emulsion. Also, the emulsions can contain additional adjuvants and additives commonly used in blood substitutes, such as salts and substances which serve to establish a physiologically acceptable pH value and/or osmotic and oncotic pressure.

The emulsions can be prepared in a known manner by conventional emulsifying techniques. For example, emulsification may be performed by ultrasonic and/or high-pressure homogenization.

The emulsions may be used in medicine as oxygen transporting blood substitutes. Also, they are usable as oxygen carrying perfusion solutions, for example for protecting exposed organs in surgery, such as protecting the myocardium against hypoxia in heart surgery. The emulsions can furthermore be used as adjuvants in diagnostics, for example for ultrasonography and $^{19}F$ NMR tomography. In biotechnology, such emulsions can be used in oxygen carrying nutrients, for example for cultivating animal and plant cells or in the synthesis of interferon.

The compounds of formula Ia or Ib or their mixtures can also be used in other fields of technology, in which liquid or waxy substances are needed which are chemically inert and/or have a capacity for dissolving gases. The compounds and mixtures are suitable, for example, as inert coolants, lubricants, sealing fluids and hydraulic fluids, insulation media in electrical engineering, and means for vapor phase soldering or as additives in agents for the above-named purposes. Because of their capacity for dissolving gases, the compounds and their mixtures are suitable as an inert medium for the diffusion of gases between different phases. Thus the compounds can also be used in processes for the technical separation of gases, such as the separation of gases by dialysis, in which the compounds serve as the inert exchange phase.

The following examples are intended to further explain the invention without, however, limiting its scope.

As electrolysis cells for the electrochemical fluorination, cells with nickel electrodes are used which have either a capacity of 300 ml and an anode surface area of 475 cm$^2$, or a capacity of 960 ml and an anode surface area of 1530 cm$^2$. The cells are provided with a reflux condenser which is maintained at a temperature between $-15°$ and $-20°$ C.

EXAMPLE 1

Preparation of a mixture of perfluorocyclohexylmorpholine and perfluoro-n-hexylmorpholine A 5% to 15% solution of morpholinecyclohexene-(1) in pre-dried, refrigerated liquid hydrogen fluoride was perfluorinated in an electrolysis cell at an anode current density of 3 to 20 mA/cm$^2$, a cell voltage of 5 to 6.5 volts and a cell temperature of -8 to +5 C. From time to time additional morpholinocyclohexene-(1) dissolved in liquid hydrogen fluoride was added and spent hydrogen fluoride replaced to enable the cell to be operated continuously. The heavy phase containing the raw reaction product, which settled on the cell bottom, was withdrawn from time to time. The raw product was treated with equal volumes of an aqueous 8N potassium hydroxide solution and dibutylamine. The mixture was heated at reflux for 8 days. Then the mixture was fractionally distilled. In the distillation a main fraction was obtained in the boiling range of 145 to 148 C, which consisted primarily of perfluorinated cyclohexylmorpholine and can be used without further purification for most of the applications referred to in the above description. The yield was 30%. Gas chromatographic analysis showed that the distillate was a mixture of 65% of the principal product, perfluorocyclohexyl morpholine, 33% of the by-product, perfluoro-n-hexylmorpholine, and 2% additional by-products, with a boiling point of 147.5°-148.5° C. and a vapor pressure of 12 torr at 37° C.

EXAMPLE 2

Preparation of a mixture of perfluorocyclohexylmorpholine and perfluoro-n-hexylmorpholine The procedure described in Example 1 was followed, but an electrolysis cell was used which was additionally provided with a circulating pump. By constantly recirculating the entire cell contents, the electrolyte was fed again and again into the electrode area during the electrolysis. For continuous operation, additional starting product was supplied from time to time as described in Example 1. The electrolysis process was followed by monitoring the changes in current and voltage. From time to time, whenever a sharp drop in conductivity indicated an increase in the concentration of perfluorinated product and a corresponding decrease in the electrolyte concentration, the circulation was interrupted and the heavy phase containing the raw product which collected on the bottom of the cell was withdrawn. The raw product was worked up as described in Example 1. The mixture obtained as distillate had the composition given in Example 1. A yield of 43% was achieved.

EXAMPLE 3

Preparation of pure perfluorocyclohexylmorpholine by separating the mixtures obtained in Examples 1 or 2

The mixture of perfluorocyclohexylmorpholine and perfluoro-n-hexylmorpholine obtained in Example. was introduced at 120° C. through an evaporator to a glass column filled with a zeolite molecular sieve having a pore size of 5 Å through which a constant stream of helium flowed at a rate of 60 ml per minute. While the perfluorocyclohexylmorpholine passed through the column, the by-product containing the $C_6F_{13}$ moiety was largely retained. Thus, pure perfluorinated cyclohexylmorpholine was obtained with a boiling point of 147.5°-149.5° C. After all of the perfluorocyclohexylmorpholine and excess-- perfluoro-n-hexylmorpholine had left the column, the temperature was increased to 300° C. In a refrigerated trap at the column outlet pure perfluoro-n-hexylmorpholine condensed, having a boiling point of 149°-150° C.

The perfluorocyclohexylmorpholine and the perfluoro-n-hexylmorpholine had a vapor pressure of 12 torr at 37° C.

The oxygen dissolving capacity ($=O_2$solv.) of the perfluorocyclohexylmorpholine and the perfluoro-n-hexylmorpholine, and their critical temperature of solution in n-hexane ($=$CTSH), which can be considered as a good index for the residince time of the perfluorocarbons in the body, were determined by the following methods:

A. Determination of the oxygen dissolving capacity

The determination was performed in a two-liter round flask provided with a valve for delivery of oxygen, a valve for evacuation, and a pressure gauge, and with a bottom extension suitable for containing the perfluorocarbon, into which the perfluorocarbon can be introduced through a septum.

The apparatus was first evacuated with a water-jet pump, filled with oxygen, evacuated again, and again filled with oxygen until an internal pressure of 1013 mbar was reached. Then the perfluorocarbon was introduced through a septum into the bottom extension and stirred there for 2 hours under an oxygen atmosphere. The temperature was maintained at 37° C. by means of a cryostat. After 2 hours part of the perfluorocarbon was removed and tested by gas chromatography for its oxygen content.

The gas chromatographic investigation was performed with a CAP 12 gas chromatograph made by Gira, France. The carrier gas was helium with a flow rate of 20 ml/min. The separating column was a glass column measuring 2 m×4 mm diameter, filled with a 5 Å molecular sieve of 40-60 mesh. The oven temperature was 100° C.; the injector temperature 250° C., and the detector temperature 200° C. The sample volume was 30 to 50 μl.

B. Determination of the critical temperature of dissolution in n-hexane.

Equal volumes (50 μl each) of the perfluorocarbon and n-hexane were melted into a glass tube (about 3 cm long, diam. 3 mm) with cooling (−70° C.). To determine the miscibility of the two liquids, the bath temperature in an apparatus for determining melting points was slowly raised and lowered, and the temperature at which the two phases mix or become visible was measured.

| Results: | $O_2$ solv. @ 37° C. | CTSH |
|---|---|---|
| Perfluorocyclohexylmorpholine | 47 vol % | 32° C. |
| Perfluoro-n-hexylmorpholine | 45 vol % | 45° C. |

The foregoing results show that the compounds are suitable for use as oxygen carrying perfluorocarbons, and that perfluorocyclohexylmorpholine has a substantially lower CTSH than perfluoro-n-hexylmorpholine. This is an indication of a half-life in the body that is well suited for use in blood substitutes.

Analogously to the methods described in the foregoing examples, perfluorocyclopentylmorpholine or perfluorocyclopentylmorpholine/ perfluoro-n-pentylmorpholine mixtures, and perfluorocyclohexylpiperidine or perfluorocyclohexylpiperidine/ perfluoro-n-hexylpiperidine mixtures, can also be obtained in good yields, of over 40% for example, by electrochemical perfluorination of corresponding starting compounds of formula II. The starting compounds of formula II can be prepared in a manner analogous to the procedure given below for preparing morpholinocyclohexene-(1).

Preparation of morpholinocyclohexene-(1)

1.2 mol of morpholine is heated with 1.0 mole cyclohexanone and 200 ml toluene on the water separator until no more water of reaction is separated. Then the compound of formula II is isolated from the reaction mixture by fractional distillation.

EXAMPLE I

Preparation of an aqueous emulsion containing a perfluorinated cyclohexylmorpholine 2 g of the perfluorinated cyclohexylmorpholine obtained in Example 2 was added to 0.3 g of the emulsifier, Pluronic ® F68 (=ethylene oxide-propylene oxide block polymer, average molecular weight 8300; from Wyandotte Chemical) and water was added to the mixture to make the total volume 10 ml. It was homogenized for 2 minutes with ultrasound. The resulting emulsion had a colloidal particle size of approximately 200 nm, which remained constant upon standing at +4° C. for several weeks.

EXAMPLE II

Aqueous emulsion containing perfluorinated cyclohexylmorpholine suitable as a blood substitute or perfusion medium

| Composition: | |
|---|---|
| Perfluorinated cyclohexylmorpholine obtained according to Example 2 | 200 g/l |
| Emulsifier (Pluronic ® F68) | 27 g/l |
| Glycerin | 8 g/l |
| Egg white phospholipids | 4 g/l |
| Hydroxyethyl starch (average molecular weight 200,000) | 30 g/l |
| Na+ | 128.0 mmol/l |
| K+ | 4.5 mmol/l |
| Ca++ | 2.5 mmol/l |
| Mg++ | 2.1 mmol/l |
| Cl− | 116.0 mmol/l |
| $HCO_3-$ | 25 mmol/l |
| Glucose | 10.0 mmol/l |
| Sterile distilled water | to make 1 liter |

The listed components were homogenized in a known manner.

The foregoing description and examples have been set forth merely to illustrate the invention and are not intended to be limiting. Since modifications of the described embodiments incorporating the spirit and substance of the invention may occur to persons skilled in the art, the scope of the invention should be construed to include all modifications falling within the ambit of the appended claims and equivalents thereof.

What is claimed is:

1. A method for preparing compounds corresponding to the formulas Ia and Ib:

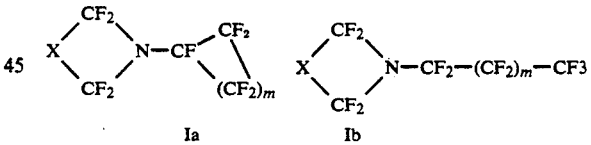

wherein m is 3 or 4 and X is a —CF₂—O—CF₂— group, a —CF₂—CF₂—CF₂— group or a —CF(CF₃)—CF₂— group, or mixtures thereof, said method comprising the steps of:

a) electrolyzing a solution of a compound corresponding to the formula II:

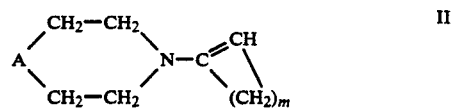

wherein m has the above meaning and A represents oxygen or a —CH₂— group, in liquid hydrogen fluoride, and separating a raw reaction product containing perfluorinated compounds of formulas Ia and Ib plus partially fluorinated by-products;

b) treating said raw reaction product with an alkali metal or alkaline earth metal base in the presence of water at an elevated temperature sufficient to decompose the partially fluorinated by-products; and c) isolating a mixture of the compounds of formulas Ia and Ib from the treated reaction product from step b).

2. A method according to claim 1, further comprising the additional step of separating the isolated mixture from step c) into the individual compounds of formulas Ia and Ib.

3. A method according to claim 2, wherein said additional separating step is performed by adsorption/desorption on a molecular sieve.

4. A method according to claim 3, wherein said molecular sieve is an inorganic molecular sieve with a pore size of from about 5 to 6.5 Å.

5. A method according to claim 1, further comprising the additional step of separating isomer mixtures of compounds of formulas Ia or Ib, wherein X is a $-CF_2-CF_2-CF_2-$ group and m has the above meaning, and compounds of formulas Ia or Ib which are isomeric therewith, wherein X is a $-CF(CF_3)-CF_2-$ group, into the individual isomers.

6. A method according to claim 5, wherein said additional separating step is performed by adsorption/desorption on a molecular sieve.

7. A method according to claim 6, wherein said molecular sieve is an inorganic molecular sieve with a pore size of from about 5 to 6.5 Å.

8. A method according to claim 1, wherein said alkali metal or alkaline earth metal base in step b) is an alkali metal or alkaline earth metal hydroxide.

9. A method according to claim 1, wherein said base treatment step b) is carried out in the presence of a lower aliphatic primary or secondary amine.

10. A method according to claim 9, wherein an aqueous alkali metal hydroxide solution and a lower aliphatic primary or secondary amine are used in said base treatment step b).

11. A method according to claim 10, wherein said amine is a secondary amine.

12. A method according to claim 11, wherein said amine is a dibutyl amine.

13. A method according to claim 1, wherein an aqueous alkali metal hydroxide solution, especially potassium hydroxide solution, is used as the base in step b).

14. A method according to claim 1, wherein the electrolysis in step a) is performed at a temperature between $-25°$ and $+10°$ C. and at a cell voltage of from 3 to 10 volts.

15. A method according to claim 14, wherein the electrolysis in step a) is performed at a temperature in the range from $-5°$ to $+5°$ C. and at a cell voltage of from 4 to 8 volts.

16. A method according to claim 1, wherein the compounds of formulas Ia and Ib or a mixture thereof are isolated in step c) from the treated reaction product from step b) by distillation.

* * * * *